US006409995B1

(12) United States Patent
Habeck et al.

(10) Patent No.: US 6,409,995 B1
(45) Date of Patent: Jun. 25, 2002

(54) USE OF AMINO-SUBSTITUTED HYDROXYBENZOPHENONES AS PHOTOSTABLE UV FILTERS IN COSMETIC AND PHARMACEUTICAL PREPARATIONS

(75) Inventors: Thorsten Habeck, Meckenheim; Frank Prechtl, Frankfurt; Thomas Wünsch, Speyer; Horst Westenfelder, Neustadt; Sylke Haremza, Neckargemünd; Thorsten Bach; Anja Spiegel, both of Marburg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/553,897

(22) Filed: Apr. 20, 2000

(30) Foreign Application Priority Data

Apr. 20, 1999 (DE) ........................................ 199 17 906

(51) Int. Cl.$^7$ ...................... C07D 493/10; C07D 97/10; C07D 69/734; C07D 101/60; B41M 5/145; B41M 5/124; C09B 11/28

(52) U.S. Cl. .......................... 424/59; 424/60; 424/70.1; 514/428; 514/534; 514/619; 548/573; 560/43; 562/441; 564/67

(58) Field of Search .......................... 548/573; 560/43; 562/441; 564/167; 424/59, 60, 70.1; 514/534, 619, 428

(56) References Cited

U.S. PATENT DOCUMENTS

| | | | | |
|---|---|---|---|---|
| 4,387,089 A | 6/1983 | De Polo | 424/59 |
| 5,576,354 A | 11/1996 | Deflandre et al. | 514/685 |
| 5,587,150 A | 12/1996 | Deflandre et al. | 424/59 |

FOREIGN PATENT DOCUMENTS

| | | |
|---|---|---|
| DE | 197 26 121 A1 | 12/1998 |
| EP | 0 251 398 | 1/1988 |
| EP | 0 416 837 A1 | 3/1991 |
| EP | 0 514 491 B1 | 11/1992 |
| FR | 2 440 933 | 6/1980 |
| JP | 63139158 | 6/1988 |
| JP | 05163275 | 6/1993 |
| WO | WO 91/11989 | 8/1991 |

OTHER PUBLICATIONS

Brown et al. "The Blue Sodium of Rhodamine–B and some Related Substances", Jnl. of Chemical Society, (1993) pp. 1264–1269.

Organikum, VEB Deutscher Verlag der Wissenschaften, Berlin 1986, pp 323–327.

Houben–Weyl, vol. 7/2a, 1973, pp 379–389.

*Primary Examiner*—Floyd D. Higel
(74) *Attorney, Agent, or Firm*—Keil & Weinkauf

(57) ABSTRACT

Use of amino-substituted hydroxybenzophenones of the formula I

I

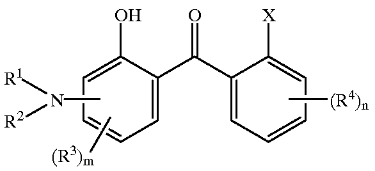

in which the variables have the meanings explained in the description, as photostable UV filters in cosmetic and pharmaceutical preparations for protecting human skin or human hair from the sun's rays, alone or together with compounds which absorb in the UV region and are known per se for cosmetic and pharmaceutical preparations.

7 Claims, No Drawings

USE OF AMINO-SUBSTITUTED HYDROXYBENZOPHENONES AS PHOTOSTABLE UV FILTERS IN COSMETIC AND PHARMACEUTICAL PREPARATIONS

The invention relates to the use of amino-substituted hydroxybenzophenones as photostable UV filters in cosmetic and pharmaceutical preparations for protecting the human epidermis or human hair from UV radiation, specifically in the range from 320 to 400 nm.

The sunscreens employed in cosmetic and pharmaceutical preparations have the task of preventing, or at least diminishing the consequences of, harmful effects of sunlight on the human skin. However, these sunscreens also serve to protect other ingredients from decomposition or -breakdown by UV radiation. In hair cosmetic formulations the aim is to reduce damage to the keratin fibers by UV rays.

The sunlight reaching the surface of the earth contains proportions of UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect using the minimum amount, sunscreens of this type ought additionally to have a high specific absorbance. Sunscreens for cosmetic products must also meet a large number of other requirements, for example good solubility in cosmetic oils, high stability of the emulsions produced with them, toxicological acceptability, and low intrinsic odor and low intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and short intervals are required if effective protection of the skin from all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 and EP-A-0 416 837 to combine chromophores absorbing UV-A radiation and UV-B radiation into one molecule using a linker. This has the disadvantage that firstly a free combination of UV-A and UV-B filters in the cosmetic preparation is no longer possible, and that difficulties in the chemical linkage of the chromophores allow only certain combinations.

It is an object of the present invention to propose sunscreens for cosmetic and pharmaceutical purposes-which absorb in the UV-A region with high absorbance, which are photostable, have low intrinsic color, i.e. a sharp band structure, and are soluble in oil or water depending on the substituent.

We have found that this object is achieved by the use of amino-substituted hydroxybenzophenones of the formula I

I

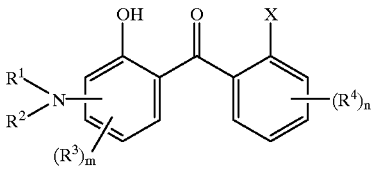

in which the variables independently of one another have the following meanings:

$R^1$ and $R^2$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, where the substituents $R^1$ and $R^2$ together with the nitrogen atom to which they are bonded can form a 5- or 6-membered ring;

$R^3$ and $R^4$ are $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, heteroaryl, optionally substituted, substituents which confer solubility in water, chosen from the group consisting of a nitrile group, carboxylate, sulfonate or ammonium radicals;

x is hydrogen, $COOR^5$, $CONR^6R^7$;

$R^5$ to $R^7$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, —(Y—O)$_o$—Z, aryl;

Y is —$(CH_2)_2$—, —$(CH_2)_3$—, —$(CH_2)_4$—, —CH$(CH_3)$—$CH_2$—;

Z is —$CH_2$13 $CH_3$, —$CH_2$13 $CH_2$13 $CH_3$, —$CH_2$—$CH_2$—$CH_2$—$CH_3$, —$CH(CH_3)$—$CH_3$;

m is from 0 to 3;

n is from 0 to 4;

o is from 1 to 20 as photostable UV filters in cosmetic and pharmaceutical preparations for protecting the human skin or human hair from the sun's rays, alone or together with compounds which absorb in the UV region and are known per se for cosmetic and pharmaceutical preparations.

Alkyl radicals $R^1$ to $R^7$ which may be mentioned are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1- dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals $R^1$ to $R^7$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^1$ to $R^7$ are preferably branched or unbranched $C_3$–$C_{10}$-cycloalkyl chains such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^1$ to $R^7$ are preferably branched or unbranched $C_3$–$C_{10}$-cycloalkenyl chains with one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be unsubstituted or substituted by one or more, e.g. 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms such as sulfur, nitrogen, whose free valences can be saturated by hydrogen or $C_1$–$C_4$-alkyl, or oxygen in the ring.

Suitable alkoxy radicals for $R^3$ and $R^4$ are those having 1 to 12 carbon atoms, preferably having 1 to 8 carbon atoms.

Examples which may be mentioned are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Examples of alkoxycarbonyl radicals for $R^3$ and $R^4$ are esters containing the abovementioned alkoxy radicals or radicals derived from higher alcohols, e.g. having up to 20 carbon atoms, such as iso-$C_{15}$ alcohol.

Suitable mono- or dialkylamino radicals for $R^3$ and $R^4$ are those containing alkyl radicals having 1 to 12 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl means aromatic rings or ring systems having 6 to 18 carbon atoms in the ring system, for example phenyl or naphthyl, each of which may be unsubstituted or substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Heteroaryl radicals are advantageously simple or fused aromatic ring systems having one or more heteroaromatic 3- to 7-membered rings. Heteroatoms which may be present in the ring or ring system are one or more nitrogen, sulfur and/or oxygen atoms. Hydrophilic radicals, i.e. those making it possible for the compounds of the formula I to dissolve in water, for $R^3$ and $R^4$ are, for example, the nitrile group and carboxyl and sulfoxy radicals and, in particular, their salts with any physiologically tolerated cations, such as the alkali metal salts or such as the trialkylammonium salts, such as tri(hydroxyalkyl)ammonium salts or the 2-methyl-1-propanol-2-ammonium salts. Also suitable are ammonium radicals, especially alkylammonium radicals, with any physiologically tolerated anions.

The substituents $R^1$ and $R^2$ can, together with the nitrogen atom to which they are bonded, form a 5- or 6-membered ring, for example a pyrrolidine or piperidine ring.

The amino group can be in the ortho, meta or para position relative to the carbonyl group. The para position is preferred.

Preference is given to compounds of the formula Ib

Ib

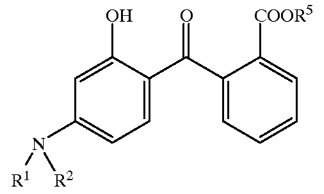

in which the substituents independently of one another have the following meanings:

$R^1$ and $R^2$ are hydrogen, $C_1$–$C_{12}$-alkyl, where the substituents $R^1$ and $R^2$ together with the nitrogen atom to which they are bonded can form a 5- or 6-membered ring;

$R^5$ is hydrogen, $C_1$–$C_{12}$-alkyl, $C_3$–$C_6$-cycloalkyl.

Alkyl radicals for $R^1$, $R^2$ and $R^5$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2trimethylpropyl, 1,2,2-trimethylpropyl, 1-ethyl-1-methylpropyl, 1-ethyl-2-methylpropyl, n-heptyl, n-octyl or 2-ethylhexyl.

Particularly preferred alkyl radicals for $R^1$, $R^2$ and $R^5$ which may be mentioned are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylhexyl.

Particularly preferred $C_3$–$C_6$-cycloalkyl radicals for $R^5$ which may be mentioned are cyclopropyl, cyclopentyl and cyclohexyl.

Furthermore, compounds of the formula Ib in which the substituents $R^1$, $R^2$ and $R^5$ are present in the combination given in Table 1 have particular photostable properties:

TABLE 1

Ib

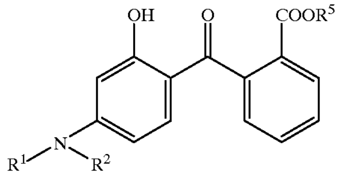

| $R^1$ | $R^2$ | $R^5$ |
|---|---|---|
| H | H | H |
| H | H | Methyl |
| H | H | Ethyl |
| H | H | n-Propyl |
| H | H | 1-Methylethyl |
| H | H | n-Butyl |
| H | H | 1-Methylpropyl |
| H | H | 2-Methylpropyl |
| H | H | 1,1-Dimethylethyl |
| H | H | n-Pentyl |
| H | H | 1-Methylbutyl |
| H | H | 2-Methylbutyl |
| H | H | 2,2-Dimethylpropyl |
| H | H | 2-Ethylhexyl |
| H | H | Cyclopropyl |
| H | H | Cyclopentyl |
| H | H | Cyclohexyl |
| Methyl | Methyl | H |
| Methyl | Methyl | Methyl |
| Methyl | Methyl | Ethyl |
| Methyl | Methyl | n-Propyl |
| Methyl | Methyl | 1-Methylethyl |
| Methyl | Methyl | n-Butyl |
| Methyl | Methyl | 1-Methylpropyl |
| Methyl | Methyl | 2-Methylpropyl |
| Methyl | Methyl | 1,1-Dimethylethyl |
| Methyl | Methyl | n-Pentyl |
| Methyl | Methyl | 1-Methylbutyl |
| Methyl | Methyl | 2-Methylbutyl |
| Methyl | Methyl | 2,2-Dimethylpropyl |
| Methyl | Methyl | 2-Ethylhexyl |
| Methyl | Methyl | Cyclopropyl |
| Methyl | Methyl | Cyclopentyl |
| Methyl | Methyl | Cyclohexyl |
| Ethyl | Ethyl | H |
| Ethyl | Ethyl | Methyl |
| Ethyl | Ethyl | Ethyl |
| Ethyl | Ethyl | n-Propyl |
| Ethyl | Ethyl | 1-Methylethyl |
| Ethyl | Ethyl | n-Butyl |
| Ethyl | Ethyl | 1-Methylpropyl |
| Ethyl | Ethyl | 2-Methylpropyl |
| Ethyl | Ethyl | 1,1-Dimethylethyl |
| Ethyl | Ethyl | n-Pentyl |
| Ethyl | Ethyl | 1-Methylbutyl |
| Ethyl | Ethyl | 2-Methylbutyl |
| Ethyl | Ethyl | 2,2-Dimethylpropyl |
| Ethyl | Ethyl | 2-Ethylhexyl |
| Ethyl | Ethyl | Cyclopropyl |
| Ethyl | Ethyl | Cyclopentyl |
| Ethyl | Ethyl | Cyclohexyl |
| n-Propyl | n-Propyl | H |
| n-Propyl | n-Propyl | Methyl |
| n-Propyl | n-Propyl | Ethyl |
| n-Propyl | n-Propyl | n-Propyl |
| n-Propyl | n-Propyl | 1-Methylethyl |
| n-Propyl | n-Propyl | n-Butyl |
| n-Propyl | n-Propyl | 1-Methylpropyl |
| n-Propyl | n-Propyl | 2-Methylpropyl |
| n-Propyl | n-Propyl | 1,1-Dimethylethyl |
| n-Propyl | n-Propyl | n-Pentyl |
| n-Propyl | n-Propyl | 1-Methylbutyl |
| n-Propyl | n-Propyl | 2-Methylbutyl |
| n-Propyl | n-Propyl | 2,2-Dimethylpropyl |
| n-Propyl | n-Propyl | 2-Ethylhexyl |
| n-Propyl | n-Propyl | Cyclopropyl |

TABLE 1-continued

Ib

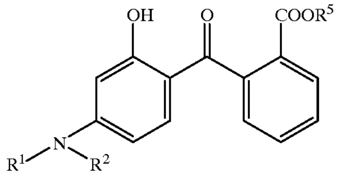

| $R^1$ | $R^2$ | $R^5$ |
|---|---|---|
| n-Propyl | n-Propyl | Cyclopentyl |
| n-Propyl | n-Propyl | Cyclohexyl |
| 1-Methylethyl | 1-Methylethyl | H |
| 1-Methylethyl | 1-Methylethyl | Methyl |
| 1-Methylethyl | 1-Methylethyl | Ethyl |
| 1-Methylethyl | 1-Methylethyl | n-Propyl |
| 1-Methylethyl | 1-Methylethyl | 1-Methylethyl |
| 1-Methylethyl | 1-Methylethyl | n-Butyl |
| 1-Methylethyl | 1-Methylethyl | 1-Methylpropyl |
| 1-Methylethyl | 1-Methylethyl | 2-Methylpropyl |
| 1-Methylethyl | 1-Methylethyl | 1,1-Dimethylethyl |
| 1-Methylethyl | 1-Methylethyl | n-Pentyl |
| 1-Methylethyl | 1-Methylethyl | 1-Methylbutyl |
| 1-Methylethyl | 1-Methylethyl | 2-Methylbutyl |
| 1-Methylethyl | 1-Methylethyl | 2,2-Dimethylpropyl |
| 1-Methylethyl | 1-Methylethyl | 2-Ethylhexyl |
| 1-Methylethyl | 1-Methylethyl | Cyclopropyl |
| 1-Methylethyl | 1-Methylethyl | Cyclopentyl |
| 1-Methylethyl | 1-Methylethyl | Cyclohexyl |
| n-Butyl | n-Butyl | H |
| n-Butyl | n-Butyl | Methyl |
| n-Butyl | n-Butyl | Ethyl |
| n-Butyl | n-Butyl | n-Propyl |
| n-Butyl | n-Butyl | 1-Methylethyl |
| n-Butyl | n-Butyl | n-Butyl |
| n-Butyl | n-Butyl | 1-Methylpropyl |
| n-Butyl | n-Butyl | 2-Methylpropyl |
| n-Butyl | n-Butyl | 1,1-Dimethylethyl |
| n-Butyl | n-Butyl | n-Pentyl |
| n-Butyl | n-Butyl | 1-Methylbutyl |
| n-Butyl | n-Butyl | 2-Methylbutyl |
| n-Butyl | n-Butyl | 2,2-Dimethylpropyl |
| n-Butyl | n-Butyl | 2-Ethylhexyl |
| n-Butyl | n-Butyl | Cyclopropyl |
| n-Butyl | n-Butyl | Cyclopentyl |
| n-Butyl | n-Butyl | Cyclohexyl |
| 1-Methylpropyl | 1-Methylpropyl | H |
| 1-Methylpropyl | 1-Methylpropyl | Methyl |
| 1-Methylpropyl | 1-Methylpropyl | Ethyl |
| 1-Methylpropyl | 1-Methylpropyl | n-Propyl |
| 1-Methylpropyl | 1-Methylpropyl | 1-Methylethyl |
| 1-Methylpropyl | 1-Methylpropyl | n-Butyl |
| 1-Methylpropyl | 1-Methylpropyl | 1-Methylpropyl |
| 1-Methylpropyl | 1-Methylpropyl | 2-Methylpropyl |
| 1-Methylpropyl | 1-Methylpropyl | 1,1-Dimethylethyl |
| 1-Methylpropyl | 1-Methylpropyl | n-Pentyl |
| 1-Methylpropyl | 1-Methylpropyl | 1-Methylbutyl |
| 1-Methylpropyl | 1-Methylpropyl | 2-Methylbutyl |
| 1-Methylpropyl | 1-Methylpropyl | 2,2-Dimethylpropyl |
| 1-Methylpropyl | 1-Methylpropyl | 2-Ethylhexyl |
| 1-Methylpropyl | 1-Methylpropyl | Cyclopropyl |
| 1-Methylpropyl | 1-Methylpropyl | Cyclopentyl |
| 1-Methylpropyl | 1-Methylpropyl | Cyclohexyl |
| 2-Methylpropyl | 2-Methylpropyl | H |
| 2-Methylpropyl | 2-Methylpropyl | Methyl |
| 2-Methylpropyl | 2-Methylpropyl | Ethyl |
| 2-Methylpropyl | 2-Methylpropyl | n-Propyl |
| 2-Methylpropyl | 2-Methylpropyl | 1-Methylethyl |
| 2-Methylpropyl | 2-Methylpropyl | n-Butyl |
| 2-Methylpropyl | 2-Methylpropyl | 1-Methylpropyl |
| 2-Methylpropyl | 2-Methylpropyl | 2-Methylpropyl |
| 2-Methylpropyl | 2-Methylpropyl | 1,1-Dimethylethyl |
| 2-Methylpropyl | 2-Methylpropyl | n-Pentyl |
| 2-Methylpropyl | 2-Methylpropyl | 1-Methylbutyl |
| 2-Methylpropyl | 2-Methylpropyl | 2-Methylbutyl |
| 2-Methylpropyl | 2-Methylpropyl | 2,2-Dimethylpropyl |

TABLE 1-continued

Ib

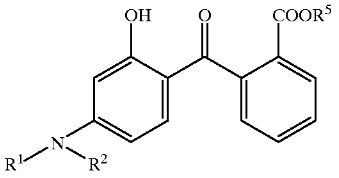

| $R^1$ | $R^2$ | $R^5$ |
|---|---|---|
| 2-Methylpropyl | 2-Methylpropyl | 2-Ethylhexyl |
| 2-Methylpropyl | 2-Methylpropyl | Cyclopropyl |
| 2-Methylpropyl | 2-Methylpropyl | Cyclopentyl |
| 2-Methylpropyl | 2-Methylpropyl | Cyclohexyl |
| 1,1-Dimethylethyl | 1,1-Dimethylethyl | H |
| 1,1-Dimethylethyl | 1,1-Dimethylethyl | Methyl |
| 1,1-Dimethylethyl | 1,1-Dimethylethyl | Ethyl |
| 1,1-Dimethylethyl | 1,1-Dimethylethyl | n-Propyl |
| 1,1-Dimethylethyl | 1,1-Dimethylethyl | 1-Methylethyl |
| 1,1-Dimethylethyl | 1,1-Dimethylethyl | n-Butyl |
| 1,1-Dimethylethyl | 1,1-Dimethylethyl | 1-Methylpropyl |
| 1,1-Dimethylethyl | 1,1-Dimethylethyl | 2-Methylpropyl |
| 1,1-Dimethylethyl | 1,1-Dimethylethyl | 1,1-Dimethylethyl |
| 1,1-Dimethylethyl | 1,1-Dimethylethyl | n-Pentyl |
| 1,1-Dimethylethyl | 1,1-Dimethylethyl | 1-Methylbutyl |
| 1,1-Dimethylethyl | 1,1-Dimethylethyl | 2-Methylbutyl |
| 1,1-Dimethylethyl | 1,1-Dimethylethyl | 2,2-Dimethylpropyl |
| 1,1-Dimethylethyl | 1,1-Dimethylethyl | 2-Ethylhexyl |
| 1,1-Dimethylethyl | 1,1-Dimethylethyl | Cyclopropyl |
| 1,1-Dimethylethyl | 1,1-Dimethylethyl | Cyclopentyl |
| 1,1-Dimethylethyl | 1,1-Dimethylethyl | Cyclohexyl |
| n-Pentyl | n-Pentyl | H |
| n-Pentyl | n-Pentyl | Methyl |
| n-Pentyl | n-Pentyl | Ethyl |
| n-Pentyl | n-Pentyl | n-Propyl |
| n-Pentyl | n-Pentyl | 1-Methylethyl |
| n-Pentyl | n-Pentyl | n-Butyl |
| n-Pentyl | n-Pentyl | 1-Methylpropyl |
| n-Pentyl | n-Pentyl | 2-Methylpropyl |
| n-Pentyl | n-Pentyl | 1,1-Dimethylethyl |
| n-Pentyl | n-Pentyl | n-Pentyl |
| n-Pentyl | n-Pentyl | 1-Methylbutyl |
| n-Pentyl | n-Pentyl | 2-Methylbutyl |
| n-Pentyl | n-Pentyl | 2,2-Dimethylpropyl |
| n-Pentyl | n-Pentyl | 2-Ethylhexyl |
| n-Pentyl | n-Pentyl | Cyclopropyl |
| n-Pentyl | n-Pentyl | Cyclopentyl |
| n-Pentyl | n-Pentyl | Cyclohexyl |
| 1-Methylbutyl | 1-Methylbutyl | H |
| 1-Methylbutyl | 1-Methylbutyl | Methyl |
| 1-Methylbutyl | 1-Methylbutyl | Ethyl |
| 1-Methylbutyl | 1-Methylbutyl | n-Propyl |
| 1-Methylbutyl | 1-Methylbutyl | 1-Methylethyl |
| 1-Methylbutyl | 1-Methylbutyl | n-Butyl |
| 1-Methylbutyl | 1-Methylbutyl | 1-Methylpropyl |
| 1-Methylbutyl | 1-Methylbutyl | 2-Methylpropyl |
| 1-Methylbutyl | 1-Methylbutyl | 1,1-Dimethylethyl |
| 1-Methylbutyl | 1-Methylbutyl | n-Pentyl |
| 1-Methylbutyl | 1-Methylbutyl | 1-Methylbutyl |
| 1-Methylbutyl | 1-Methylbutyl | 2-Methylbutyl |
| 1-Methylbutyl | 1-Methylbutyl | 2,2-Dimethylpropyl |
| 1-Methylbutyl | 1-Methylbutyl | 2-Ethylhexyl |
| 1-Methylbutyl | 1-Methylbutyl | Cyclopropyl |
| 1-Methylbutyl | 1-Methylbutyl | Cyclopentyl |
| 1-Methylbutyl | 1-Methylbutyl | Cyclohexyl |
| 2-Methylbutyl | 2-Methylbutyl | H |
| 2-Methylbutyl | 2-Methylbutyl | Methyl |
| 2-Methylbutyl | 2-Methylbutyl | Ethyl |
| 2-Methylbutyl | 2-Methylbutyl | n-Propyl |
| 2-Methylbutyl | 2-Methylbutyl | 1-Methylethyl |
| 2-Methylbutyl | 2-Methylbutyl | n-Butyl |
| 2-Methylbutyl | 2-Methylbutyl | 1-Methylpropyl |
| 2-Methylbutyl | 2-Methylbutyl | 2-Methylpropyl |
| 2-Methylbutyl | 2-Methylbutyl | 1,1-Dimethylethyl |
| 2-Methylbutyl | 2-Methylbutyl | n-Pentyl |
| 2-Methylbutyl | 2-Methylbutyl | 1-Methylbutyl |

TABLE 1-continued

Ib

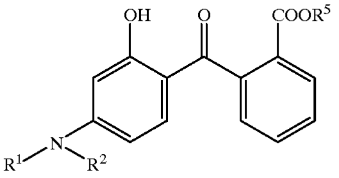

| $R^1$ | $R^2$ | $R^5$ |
|---|---|---|
| 2-Methylbutyl | 2-Methylbutyl | 2-Methylbutyl |
| 2-Methylbutyl | 2-Methylbutyl | 2,2-Dimethylpropyl |
| 2-Methylbutyl | 2-Methylbutyl | 2-Ethylhexyl |
| 2-Methylbutyl | 2-Methylbutyl | Cyclopropyl |
| 2-Methylbutyl | 2-Methylbutyl | Cyclopentyl |
| 2-Methylbutyl | 2-Methylbutyl | Cyclohexyl |
| 2,2-Dimethylpropyl | 2,2-Dimethylpropyl | H |
| 2,2-Dimethylpropyl | 2,2-Dimethylpropyl | Methyl |
| 2,2-Dimethylpropyl | 2,2-Dimethylpropyl | Ethyl |
| 2,2-Dimethylpropyl | 2,2-Dimethylpropyl | n-Propyl |
| 2,2-Dimethylpropyl | 2,2-Dimethylpropyl | 1-Methylethyl |
| 2,2-Dimethylpropyl | 2,2-Dimethylpropyl | n-Butyl |
| 2,2-Dimethylpropyl | 2,2-Dimethylpropyl | 1-Methylpropyl |
| 2,2-Dimethylpropyl | 2,2-Dimethylpropyl | 2-Methylpropyl |
| 2,2-Dimethylpropyl | 2,2-Dimethylpropyl | 1,1-Dimethylethyl |
| 2,2-Dimethylpropyl | 2,2-Dimethylpropyl | n-Pentyl |
| 2,2-Dimethylpropyl | 2,2-Dimethylpropyl | 1-Methylbutyl |
| 2,2-Dimethylpropyl | 2,2-Dimethylpropyl | 2-Methylbutyl |
| 2,2-Dimethylpropyl | 2,2-Dimethylpropyl | 2,2-Dimethylpropyl |
| 2,2-Dimethylpropyl | 2,2-Dimethylpropyl | 2-Ethylhexyl |
| 2,2-Dimethylpropyl | 2,2-Dimethylpropyl | Cyclopropyl |
| 2,2-Dimethylpropyl | 2,2-Dimethylpropyl | Cyclopentyl |
| 2,2-Dimethylpropyl | 2,2-Dimethylpropyl | Cyclohexyl |
| 2-Ethylhexyl | 2-Ethylhexyl | H |
| 2-Ethylhexyl | 2-Ethylhexyl | Methyl |
| 2-Ethylhexyl | 2-Ethylhexyl | Ethyl |
| 2-Ethylhexyl | 2-Ethylhexyl | n-Propyl |
| 2-Ethylhexyl | 2-Ethylhexyl | 1-Methylethyl |
| 2-Ethylhexyl | 2-Ethylhexyl | n-Butyl |
| 2-Ethylhexyl | 2-Ethylhexyl | 1-Methylpropyl |
| 2-Ethylhexyl | 2-Ethylhexyl | 2-Methylpropyl |
| 2-Ethylhexyl | 2-Ethylhexyl | 1,1-Dimethylethyl |
| 2-Ethylhexyl | 2-Ethylhexyl | n-Pentyl |
| 2-Ethylhexyl | 2-Ethylhexyl | 1-Methylbutyl |
| 2-Ethylhexyl | 2-Ethylhexyl | 2-Methylbutyl |
| 2-Ethylhexyl | 2-Ethylhexyl | 2,2-Dimethylpropyl |
| 2-Ethylhexyl | 2-Ethylhexyl | 2-Ethylhexyl |
| 2-Ethylhexyl | 2-Ethylhexyl | Cyclopropyl |
| 2-Ethylhexyl | 2-Ethylhexyl | Cyclopentyl |
| 2-Ethylhexyl | 2-Ethylhexyl | Cyclohexyl |
| Cyclopropyl | Cyclopropyl | H |
| Cyclopropyl | Cyclopropyl | Methyl |
| Cyclopropyl | Cyclopropyl | Ethyl |
| Cyclopropyl | Cyclopropyl | n-Propyl |
| Cyclopropyl | Cyclopropyl | 1-Methylethyl |
| Cyclopropyl | Cyclopropyl | n-Butyl |
| Cyclopropyl | Cyclopropyl | 1-Methylpropyl |
| Cyclopropyl | Cyclopropyl | 2-Methylpropyl |
| Cyclopropyl | Cyclopropyl | 1,1-Dimethylethyl |
| Cyclopropyl | Cyclopropyl | n-Pentyl |
| Cyclopropyl | Cyclopropyl | 1-Methylbutyl |
| Cyclopropyl | Cyclopropyl | 2-Methylbutyl |
| Cyclopropyl | Cyclopropyl | 2,2-Dimethylpropyl |
| Cyclopropyl | Cyclopropyl | 2-Ethylhexyl |
| Cyclopropyl | Cyclopropyl | Cyclopropyl |
| Cyclopropyl | Cyclopropyl | Cyclopentyl |
| Cyclopropyl | Cyclopropyl | Cyclohexyl |
| Cyclopentyl | Cyclopentyl | H |
| Cyclopentyl | Cyclopentyl | Methyl |
| Cyclopentyl | Cyclopentyl | Ethyl |
| Cyclopentyl | Cyclopentyl | n-Propyl |
| Cyclopentyl | Cyclopentyl | 1-Methylethyl |
| Cyclopentyl | Cyclopentyl | n-Butyl |
| Cyclopentyl | Cyclopentyl | 1-Methylpropyl |
| Cyclopentyl | Cyclopentyl | 2-Methylpropyl |
| Cyclopentyl | Cyclopentyl | 1,1-Dimethylethyl |

TABLE 1-continued

Ib

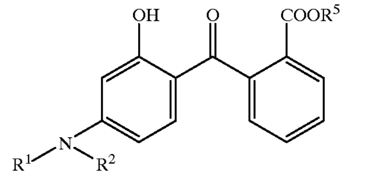

| $R^1$ | $R^2$ | $R^5$ |
|---|---|---|
| Cyclopentyl | Cyclopentyl | n-Pentyl |
| Cyclopentyl | Cyclopentyl | 1-Methylbutyl |
| Cyclopentyl | Cyclopentyl | 2-Methylbutyl |
| Cyclopentyl | Cyclopentyl | 2,2-Dimethylpropyl |
| Cyclopentyl | Cyclopentyl | 2-Ethylhexyl |
| Cyclopentyl | Cyclopentyl | Cyclopropyl |
| Cyclopentyl | Cyclopentyl | Cyclopentyl |
| Cyclopentyl | Cyclopentyl | Cyclohexyl |
| Cyclohexyl | Cyclohexyl | H |
| Cyclohexyl | Cyclohexyl | Methyl |
| Cyclohexyl | Cyclohexyl | Ethyl |
| Cyclohexyl | Cyclohexyl | n-Propyl |
| Cyclohexyl | Cyclohexyl | 1-Methylethyl |
| Cyclohexyl | Cyclohexyl | n-Butyl |
| Cyclohexyl | Cyclohexyl | 1-Methylpropyl |
| Cyclohexyl | Cyclohexyl | 2-Methylpropyl |
| Cyclohexyl | Cyclohexyl | 1,1-Dimethylethyl |
| Cyclohexyl | Cyclohexyl | n-Pentyl |
| Cyclohexyl | Cyclohexyl | 1-Methylbutyl |
| Cyclohexyl | Cyclohexyl | 2-Methylbutyl |
| Cyclohexyl | Cyclohexyl | 2,2-Dimethylpropyl |
| Cyclohexyl | Cyclohexyl | 2-Ethylhexyl |
| Cyclohexyl | Cyclohexyl | Cyclopropyl |
| Cyclohexyl | Cyclohexyl | Cyclopentyl |
| Cyclohexyl | Cyclohexyl | Cyclohexyl |

The compounds given in Table I have a photostability of >95%, preferably >98%.

The invention also relates to amino-substituted hydroxybenzophenones of the formula Ic, Ic

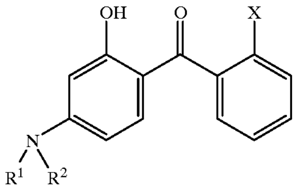

in which the variables independently of one another have the following meanings:

$R^1$ and $R^2$ are hydrogen, $C_1$–$C_8$-alkyl, where the substituents $R^1$ and $R^2$ together with the nitrogen atom to which they are bonded can form a 5- or 6-membered ring;

X is $COOR^5$, $CONR^6R^7$;

$R^5$ is $C_2$–$C_{12}$-alkyl, $C_5$–$C_6$-cycloalkyl;

$R^6$ and $R^7$ are hydrogen; $C_1$–$C_{12}$-alkyl, $C_5$–$C_6$-cycloalkyl.

Alkyl radicals $R^1$ and $R^2$ which may be mentioned are branched or unbranched $C_1$–$C_8$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or 2-ethylhexyl.

Alkyl radicals $R^5$ which may be mentioned are branched or unbranched $C_2$–$C_{12}$-alkyl chains, preferably ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl or n-dodecyl.

Alkyl radicals $R^6$ and $R^7$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or 2-ethylhexyl.

Cycloalkyl radicals which may be mentioned for $R^5$ to $R^7$ are, preferably, branched or unbranched $C_5$–$C_6$-cycloalkyl chains, such as cyclopentyl or cyclohexyl.

Preference is given to compounds of the formula Ic, in which independently of one another $R^1$ and $R^2$ are $C_1$–$C_4$-alkyl, $R^5$ is $C_3$–$C_8$-alkyl, and $R^6$ and $R^7$ are $C_1$–$C_8$-alkyl.

Particular preference is given to compounds of the formula Ic in which independently of one another $R^1$ and $R^2$ are ethyl, $R^5$ is $C_5$–$C_8$-alkyl, and $R^6$ and $R^7$ are $C_1$14 $C_8$-alkyl from the listings of the substituents, given above, in each case.

The compounds of the formula I to be used according to the invention can be prepared by direct acylation of the corresponding amino-substituted phenols.

Thus, for example, the synthesis of methyl 2-(4-dimethylamino-2-hydroxybenzoyl)benzoate (1) or methyl 2-(2-hydroxy-4-pyrrolidin-1-ylbenzoyl)benzoate (2) can be carried out by acylation of meta-diethylaminophenol or 3-pyrrolidin-1-ylphenol respectively with phthalic anhydride, and subsequent esterification.

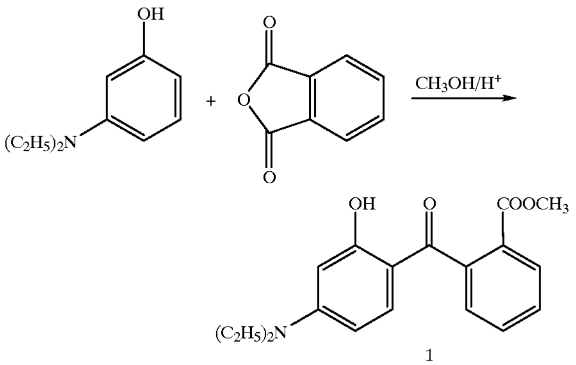

1

-continued

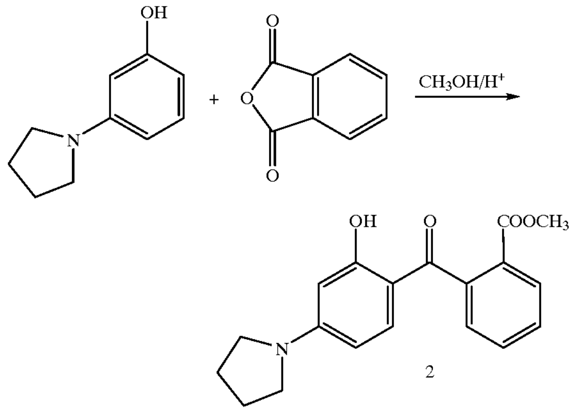

2

In addition, (4-diethylamino-2-hydroxylbenzoyl) phenylmethanone (3) can, for example, be prepared by reaction of meta-diethylaminophenol with benzoyl chloride and subsequent Fries rearrangement with $AlCl_3$.

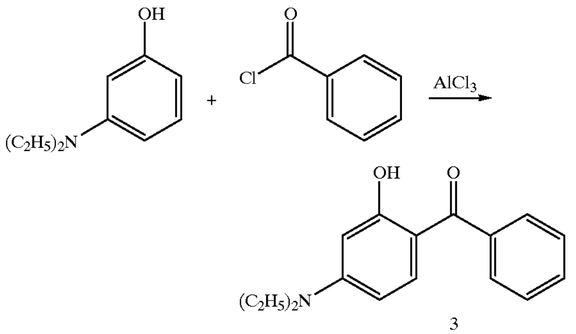

3

Details on the Friedel-Crafts reaction and on Fries's rearrangement can be found in Organikum, VEB Deutscher Verlag der Wissenschaften, Berlin, 1986, pp. 323–327, and in Houben-Weyl, Vol. 7/2a, 1973, pp. 379–389.

The present invention also relates to cosmetic and pharmaceutical preparations which comprise from 0.1 to 10% by weight, preferably 1 to 7% by weight, based on the total amount of the cosmetic and pharmaceutical preparation, of one or more of the compounds of the formula I together with compounds which absorb in the UV-A and UV-B regions and are known per se for cosmetic and pharmaceutical preparations as sunscreens, where the compounds of the formula I are generally employed in a smaller amount than the UV-B-absorbing compounds.

The sunscreen-containing cosmetic and pharmaceutical preparations are, as a rule, based on a carrier which comprises at least one oil phase. However, preparations with an exclusively aqueous basis are also possible if compounds having hydrophilic substituents are used. Accordingly, oils, oil-in-water and water-in-oil emulsions, creams and pastes, protective lipstick compositions or fat-free gels are suitable.

Suitable emulsions are inter alia also O/W macroemulsions, O/W microemulsions or O/W/O emulsions containing amino-substituted hydroxybenzophenones of the formula I in dispersed form, the emulsions being obtainable by phase inversion technology, as in DE-A-197 26 121.

Conventional cosmetic ancillary substances which may be suitable as additives are, for example, coemulsifiers, fats and waxes, stabilizers, thickeners, biogenic active substances, film formers, fragrances, dyes, pearlizing agents, preservatives, pigments, electrolytes (e.g. magnesium sulfate) and pH regulators. Suitable and preferred coemulsifiers are known W/O as well as O/W emulsifiers such as polyglycerol esters, sorbitan esters or partially esterified glycerides. Typical examples of fats are glycerides; waxes which may be mentioned are, inter alia, beeswax, paraffin wax or microwaxes, possibly combined with hydrophilic waxes. Stabilizers which can be employed are metal salts of fatty acids such as, for example, magnesium, aluminum and/or zinc stearate. Examples of suitable thickeners are crosslinked polyacrylic acids and their derivatives, polysaccharides, in particular xanthan gum, guar-guar, agar-agar, alginates and tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters such as ethylene glycol distearate, but also fatty acids and fatty acid monoglycol esters. Dyes which can be used are the substances suitable and approved for cosmetic purposes, as tabulated, for example, in the publication "Kosmetische Färbemittel" of the Farbstoffkommission der Deutschen Forschungsgemeinschaft, published by Verlag Chemie, Weinheim, 1984. These dyes are normally employed in a concentration of from 0.001 to 0.1% of the total weight of the mixture.

An additional content of antioxidants is generally preferred. Thus, it is possible to use as favorable antioxidants all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximines, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. ascorbyl palmitate, Mg ascorbylphosphate, ascorbylacetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glycosylrutin, ferulic acid, fufurylideneglucitol, carnosine, butylhydroxytoluene, butylhydroxyanisole, nordihydroguaiac acid, nordihydroguaiaretic acid, trihydroxybutyrophenone, ureic acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide).

The amount of the abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are used as the antioxidant(s), it is advantageous to choose their particular concentration from the range from 0.001 to 10% by weight, based on the total weight of the formulation.

If vitamin A and/or derivatives thereof, or carotenoids are the antioxidant(s), it is advantageous to use their particular concentration from the range from 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Such sunscreen preparations can accordingly be in liquid, paste or solid form, for example as water-in-oil creams, oil-in-water creams and lotions, aerosol foam creams, gels, oils, marking pencils, powders, sprays or alcoholic-aqueous lotions.

Finally, it is also possible to use other substances which absorb in the UV region and are known per se as long as they are stable in the overall system of the combination of UV filters to be used according to the invention.

Most of the sunscreens in the cosmetic and pharmaceutical preparations used for protecting the human epidermis consist of compounds which absorb UV light in the UV-B region, i.e. in the range from 280 to 320 nm. The content of UV-A absorbers to be used according to the invention is, for example, from 10 to 90%, by weight, preferably 20 to 50% by weight, based on the total 45 amount of UV-B- and UV-A-absorbing substances.

Any V-A and UV-B filter substances are suitable as UV filter substances which are used in combination with the compounds of the formula I to be used according to the invention. Examples which may be mentioned are:

| No. | Substance | Cas No. (=acid) |
|---|---|---|
| 1 | 4-Aminobenzoic acid | 150-13-0 |
| 2 | 3-(4-Trimethylammonium)benzylidenebornan-2-one methylsulfate | 52793-97-2 |

-continued

| No. | Substance | Cas No. (=acid) |
|---|---|---|
| 3 | 3,3,5-Trimethyl-cyclohexyl-salicylate (homosalate) | 118-56-9 |
| 4 | 2-Hydroxy-4-methoxy-benzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylene-dimethine)bis(7,7-dimethyl-2-oxobicyclo[2.2.1]-heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxy-benzophenone-5-sulfonic acid (sulisobenzone) and the sodium salt | 4065-45-6 |
| 13 | 3-(4'-Sulfo)benzylidenebornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-trianiline(o-carbo-2'-ethylhexyl-1'-oxy)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl-o-aminobenzoate or: 5-methyl-2-(1-methylethyl)-2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4'Sulfo)benzylidenebornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | 2,2'-Methylenebis-[6(2H-benzotriazol-2-yl)-4-(1,1,3,3,-tetramethylbutyl)phenol] | 103597-45-1 |
| 31 | 2,2'-(1,4-phenyl-ene)-bis-1H-benzimidazole-4,6-disulfonic acid, Na salt | 180898-37-7 |
| 32 | 2,4-bis-[4-(2-ethylhexyloxy)-2-hydroxylphenyl-6-(4-methoxy-phenyl)-(1,3,5)triazine | 187393-00-6 |

The cosmetic and dermatological preparations according to the invention can advantageously further comprise inorganic pigments based on metal oxides and/or other metal compounds which are insoluble or virtually insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and admixtures of such oxides. Particular preference is given to pigments based on $TiO_2$ and ZnO.

For the purposes of the present invention, it is particularly advantageous, but not obligatory, for the inorganic pigments to be present in hydrophobic form, i.e. to have been treated on the surface to repel water. This surface treatment can involve providing the pigments with a thin hydrophobic layer in a manner known per se, as described in DE-A-33 14 742.

To protect human hair against UV rays, the light protection agents of the formula I according to the invention can be incorporated into shampoos, lotions, gels, hairsprays, aerosol foam creams or emulsions in concentrations of from 0.1 to 10% by weight, preferably from 1 to 7% by weight. The respective formulations can be used, inter alia, for washing, coloring and for styling the hair.

The compounds to be used according to the invention are generally notable for particularly high absorbency in the region of UV-A radiation with a sharp band structure. Furthermore, they are readily soluble in cosmetic oils and can be readily incorporated into cosmetic formulations. The emulsions prepared with the compounds I are notable in particular for their high stability, the compounds I themselves for their high photostability, and the preparations prepared with I for their pleasant feel on the skin.

The UV filter action of the compounds according to the invention of the formula I can also be utilized for stabilizing active ingredients and auxiliaries in cosmetic and pharmaceutical formulations.

The examples below illustrate the preparation and use of the amino-substituted hydroxybenzophenones in more detail.

EXAMPLES

I. Preparation

Example 1

Preparation of Methyl 2-(4-diethylamino-2-hydroxybenzoyl)benzoate

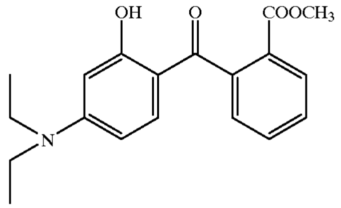

A solution of 3.11 g (18.8 mmol) of 3-diethylaminophenol and 2.88 g (19.4 mmol) of phthalic anhydride in 60 ml of abs. toluene was refluxed for 21 h. After the solvent had been removed under reduced pressure, the residue was dissolved in 100 ml of chloroform. The organic phase was washed with 6x20 ml of dilute hydrochloric acid and with 1x20 ml of water, then extracted with 6x20 ml of saturated sodium hydrogencarbonate solution. The combined aqueous extracts were acidified to pH<2 using dilute sulfuric acid and extracted with 3x50 ml of diethyl ether. The combined ether extracts were washed with 3x50 ml of water and extracted with 3x50 ml of saturated sodium hydrogencarbonate solution. The combined aqueous extracts were acidified to pH<2 and extracted with 3x50 ml of diethyl ether. The organic phases were combined, washed with 50 ml of water, dried over magnesium sulfate and filtered, and the solvent was removed under reduced pressure.

The crude product was dissolved in 40 ml of abs. methanol and 1 ml of conc. sulfuric acid and refluxed for 19 h. The solvent was removed under reduced pressure, and the residue was taken up in ethyl acetate. Washing with saturated sodium hydrogencarbonate solution and water, drying over sodium sulfate, filtration and removal of the solvent gave an oil which was purified by flash chromatography (eluent: pentane/ethyl acetate 80:20). This gave 0.77 g (2.4 mmol) of methyl 2-(4-diethylamino-2-hydroxybenzoyl)benzoate the structure of which was confirmed by NMR spectroscopy. $\lambda_{max}$: 354 nm; $E^1_1$: 1173.

Example 2

Preparation of 4-diethylamino-2-hydroxyphenyl phenyl ketone

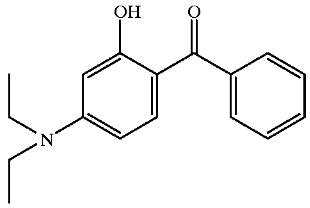

A solution of 2.99 g (18.1 mmol) of 3-diethylaminophenol, 2.7 ml (23.6 mmol) of benzoyl chloride and 2 ml of pyridine in 100 ml of abs. toluene was refluxed for 3 h. After the solvent had been removed under reduced pressure, the crude product was purified by means of flash chromatography (eluent: pentane/ethyl acetate 90:10). This gave 0.8 g of (3-diethylamino)phenyl benzoate. b)

0.78 g (2.9 mmol) of (3-diethylamino)phenyl benzoate and 1.16 g (8.7 mmol) of aluminum trichloride were mixed and heated at 175° C. for 4 h. After cooling, the reaction mixture was hydrolyzed with iced water and 2 ml of conc. hydrochloric acid. The mixture was stirred at room temperature for 1 h before 50 ml of dichloromethane were added to the reaction mixture. The organic phase was separated off, and the aqueous phase was extracted with 2x10 ml of dichloromethane. The combined organic phases were dried over sodium sulfate and filtered, and the solvent was removed under reduced pressure. The crude product was purified by flash chromatography (eluent: pentane/methyl tert-butyl ether 90:10). This gave 0.22 g of 4-diethylamino-2-hydroxyphenyl phenyl ketone. m.p.: 46–48° C.; $\lambda_{max}$: 359 nm; $E^1_1$: 1280.

Example 3

Preparation of 2-(2-hydroxy-4-pyrrolidin-1-ylbenzene)benzoic acid

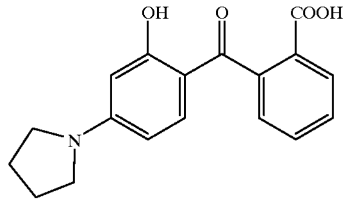

3.48 g (21.3 mmol) of 3-pyrrolidin-1-ylphenol were dissolved in 60 ml of abs. toluene. After 3.47 g (23.4 mmol) of phthalic anhydride had been added, the reaction mixture was refluxed for 22 h. After cooling, the solvent was removed under reduced pressure, and the residue was taken up in 100 ml of chloroform. The organic phase was washed with 6x20 ml of dilute hydrochloric acid and then with an amount of water such that the aqueous phase contained virtually no more rhodamine dye. The organic phase was extracted with 6x20 ml of saturated sodium hydrogencarbonate solution. The combined aqueous extracts were acidified (pH<2) using dilute sulfuric acid and extracted with 3x50 ml of ether. The combined organic phases were washed with water, dried over magnesium sulfate and filtered, and the solvent was removed under reduced pressure. This gave 4.22 g (13.5 mmol) of 2-(2-hydroxy-4-pyrrolidin-1-ylbenzene)benzoic acid as solid.

m.p.: 203° C.: $\lambda_{max}$: 355 nm; $E^1_1$: 1167.

Example 4

Preparation of methyl 2-(2-hydroxy-4-pyrrolidin-1-ylbenzene)benzoate

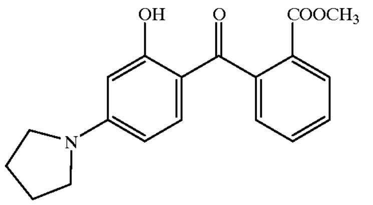

1 ml of conc. hydrochloric acid was added dropwise to a solution of 1.32 g (4.2 mmol) of 2-(2-hydroxy-4-pyrrolidin-1-ylbenzene)benzoic acid in 40 ml of abs. methanol. The reaction mixture was refluxed for 16 h. The solvent was removed under reduced pressure. The residue was taken up in 100 ml of ethyl acetate, washed with saturated sodium hydrogencarbonate solution and water, dried over sodium sulfate and filtered, and the solvent was removed under reduced pressure. The crude product was purified by flash chromatography (eluent: pentane/methyl tert-butyl ether 50:50). This gave 1.14 g (3.5 mmol) of methyl 2-(2-hydroxy-4-pyrrolidin-1-ylbenzene)benzoate. m.p.: 164° C.: $\lambda_{max}$: 355 nm; $E^1_1$: 1179.

Compounds 1 to 8 in Table 2 were prepared analogously to the examples given above.

TABLE 2

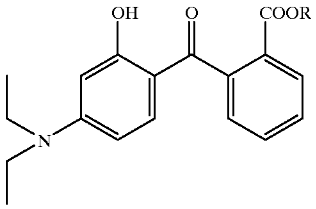

| No. | R | λmax (nm) | $E^1_1$ |
|---|---|---|---|
| 1) | Hydrogen | 354 | 1139 |
| 2) | Isobutyl | 354 | 985 |
| 3) | 2-Ethylhexyl | 345 | 902 |
| 4) | Cyclohexyl | 353 | 941 |
| 5) | Hexyl | 355 | 945 |

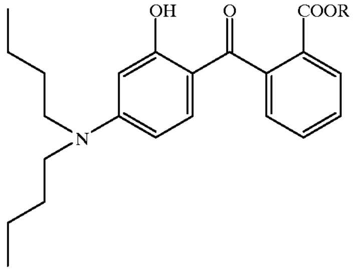

| | | | |
|---|---|---|---|
| 6) | Hydrogen | 356 | 989 |

TABLE 2-continued

| | | | |
|---|---|---|---|
| 7) | Methyl | 356 | 997 |
| 8) | Isobutyl | 356 | 908 |

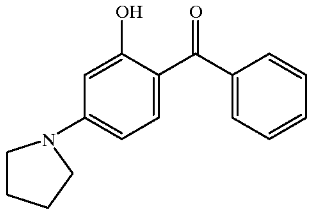

| No. | λmax (nm) | $E^1_1$ |
|---|---|---|
| 9) | 362 | 1313 |

Example 5

Standardized Method to Determine Photostability (Sun Test)

A 5% by weight alcoholic solution of the sunscreen to be tested is applied, using an Eppendorf pipette (20 μl), to the milled area on a small glass plate. Owing to the presence of the alcohol, the solution is distributed uniformly on the roughened glass surface. The amount applied corresponds to the amount of sunscreen required to obtain an average sun protection factor in sun creams. In the test, 4 small glass plates are irradiated each time. The evaporation time and the irradiation each last for 30 minutes. The glass plates are cooled slightly during the irradiation by a water cooling system located at the base of the sun test apparatus. The temperature inside the sun test apparatus during the irradiation is 40° C. After the samples have been irradiated, they are washed with ethanol into a dark 50 ml graduated flask and measured using a photometer. The blank samples are applied in the same way to small glass plates and evaporated at room temperature for 30 minutes. Like the other samples, they are washed off with ethanol and diluted to 100 ml and measured.

General Procedure for Preparing Emulsions for Cosmetic Purposes

All of the oil-soluble ingredients are heated to 85° C. in a stirred vessel. When all the ingredients have melted or are present as liquid phase, the aqueous phase is incorporated by homogenization. The emulsion is cooled to about 40° C. with stirring, is perfumed and homogenized, and is then cooled to 25° C. while stirring continuously.

Preparations

Example 6

Lip Care Composition

Mass Content (% by weight)

| Mass content (% by weight) | |
|---|---|
| ad 100 | eucerinum anhydricum |
| 10.00 | glycerol |
| 10.00 | titanium dioxide, micronized |
| 5.00 | compound No. 2 in Table 2 |
| 8.00 | octyl methoxycinnamate |
| 5.00 | zinc oxide |
| 4.00 | castor oil |
| 4.00 | pentaerythrityl stearate/caprate/caprylate/adipate |

-continued

| Mass content (% by weight) | |
|---|---|
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 7

Lip Care Composition

Mass Content (% by weight)

| Mass content (% by weight) | |
|---|---|
| ad 100 | eucerinum anhydricum |
| 10.00 | glycerol |
| 10.00 | titanium dioxide, micronized |
| 5.00 | compound No. 3 in Table 2 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 8

Sunblocker Composition Containing Micropigments

Mass Content (% by weight)

| Mass content (% by weight) | |
|---|---|
| ad 100 | water |
| 10.00 | octyl methoxycinnamate |
| 6.00 | PEG-7 hydrogenated castor oil |
| 6.00 | titanium dioxide, micronized |
| 5.00 | compound No. 2 in Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

Example 9

Sunblocker Composition Containing Micropigments

Mass Content (% by weight)

| Mass content (% by weight) | |
|---|---|
| ad 100 | water |
| 10.00 | octyl methoxycinnamate |
| 6.00 | PEG-7 hydrogenated castor oil |
| 6.00 | titanium dioxide, micronized |
| 5.00 | compound No. 3 in Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

Example 10

Non-greasy Gel

Mass Content (% by weight)

| Mass content (% by weight) | |
|---|---|
| ad 100 | water |
| 8.00 | octyl methoxycinnamate |
| 7.00 | titanium dioxide, micronized |
| 5.00 | compound No. 2 in Table 2 |
| 5.00 | glycerol |
| 5.00 | PEG-25 PABA |
| 1.00 | 4-methylbenzylidenecamphor |
| 0.40 | acrylate $C_{10}$–$C_{30}$ alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

Example 11

Non-greasy Gel

Mass Content (% by weight)

| Mass content (% by weight) | |
|---|---|
| ad 100 | water |
| 8.00 | octyl methoxycinnamate |
| 7.00 | titanium dioxide, micronized |
| 5.00 | compound No. 3 in Table 2 |
| 5.00 | glycerol |
| 5.00 | PEG-25 PABA |
| 1.00 | 4-methylbenzylidenecamphor |
| 0.40 | acrylate $C_{10}$–$C_{30}$ alkyl acrylate crosspolymer |
| 0.30 | imidazolidinylurea |
| 0.25 | hydroxyethylcellulose |
| 0.25 | sodium methylparaben |

-continued

| Mass content (% by weight) | |
|---|---|
| 0.20 | disodium EDTA |
| 0.15 | fragrance |
| 0.15 | sodium propylparaben |
| 0.10 | sodium hydroxide |

Example 12

Sun Cream (SPF 20)

Mass Content (% by weight)

| Mass content (% by weight) | |
|---|---|
| ad 100 | water |
| 8.00 | octyl methoxycinnamate |
| 8.00 | titanium dioxide, micronized |
| 6.00 | PEG-7 hydrogenated castor oil |
| 5.00 | compound No. 2 from Table 2 |
| 6.00 | mineral oil |
| 5.00 | zinc oxide |
| 5.00 | isopropyl palmitate |
| 0.30 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 13

Sun Cream (SPF 20)

Mass Content (% by weight)

| Mass content (% by weight) | |
|---|---|
| ad 100 | water |
| 8.00 | octyl methoxycinnamate |
| 8.00 | titanium dioxide, micronized |
| 6.00 | PEG-7 hydrogenated castor oil |
| 5.00 | compound No. 3 in Table 2 |
| 6.00 | mineral oil |
| 5.00 | zinc oxide |
| 5.00 | isopropyl palmitate |
| 0.30 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 14

Water-resistant Sun Cream

Mass Content (% by weight)

| Mass content (% by weight) | |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 2 in Table 2 |
| 4.00 | glycerol |
| 3.00 | jojoba oil |
| 2.00 | 4-methylbenzylidenecamphor |
| 2.00 | titanium dioxide, micronized |
| 1.50 | PEG-45/dodecyl glycol copolymer |
| 1.50 | dimethicone |
| 0.70 | magnesium sulfate |
| 0.50 | magnesium stearate |
| 0.15 | fragrance |

Example 15

Water-resistant Sun Cream

Mass Content (% by weight)

| Mass content (% by weight) | |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 3 in Table 2 |
| 4.00 | glycerol |
| 3.00 | jojoba oil |
| 2.00 | 4-methylbenzylidenecamphor |
| 2.00 | titanium dioxide, micronized |
| 1.50 | PEG-45/dodecyl glycol copolymer |
| 1.50 | dimethicone |
| 0.70 | magnesium sulfate |
| 0.50 | magnesium stearate |
| 0.15 | fragrance |

Example 16

Sun Milk (SPF 6)

Mass Content (% by weight)

| Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound No. 2 in Table 2 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |

-continued

| Mass content (% by weight) | |
|---|---|
| 0.15 | propylparaben |
| 0.05 | tocopherol |

Example 17

Sun Milk (SPF 6)
Mass Content
(% by weight)

| Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound No. 3 in Table 2 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

We claim:

1. A method of protecting human skin or human hair from UV-radiation comprising treating said hair or skin with an effective amount of a cosmetic or a pharmaceutical formulation containing an amino-substituted hydroxybenzophenone of formula I

I

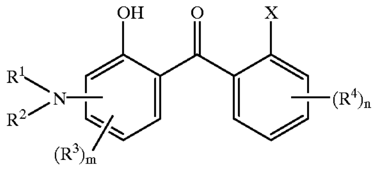

in which the variables independently of one another have the following meanings:

$R^1$ and $R^2$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, where the substituents $R^1$ and $R^2$ together with the nitrogen atom to which they are bonded can form a 5- or 6-membered ring;

$R^3$ and $R^4$ are $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, heteroaryl, optionally substituted, substituents which confer solubility in water, chosen from the group consisting of a nitrile group, carboxylate, sulfonate or ammonium radicals;

X is hydrogen, $COOR^5$, $CONR^6R^7$;

$R^5$ to $R^7$ are hydrogen, $C_1$–$C_{20}$-alkyl, $C_2$–$C_{10}$-alkenyl, $C_3$14 $C_{10}$-cycloalkyl, $C_3$–$C_{10}$-cycloalkenyl, $-(Y-O)_o-Z$,aryl;

Y is $-(CH_2)_2-$, $-(CH_2)_3-$, $-(CH_2)_4-$, $-CH(CH_3)-CH_2-$;

Z is $-CH_2-CH_3$, $-CH_2-CH_2-CH_3$, $-CH_2-CH_2-CH_2-CH_3$, $-CH(CH_3)-CH_3$;

m is from 0 to 3;

n is from 0 to 4;

is from 1 to 20 as a photostable UV filter.

2. The method of claim 1, wherein the compounds of formula I are photostable UV-A filters.

3. The method of claim 1 wherein the compounds of formula I act as UV stabilizers.

4. The method of claim 1, wherein the amino-substituted hydroxybenzophenone has the formula Ib, Ib

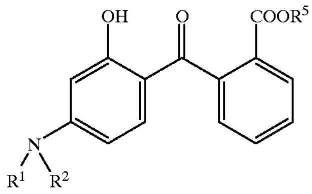

in which the substituents independently of one another have the following meanings:

$R^1$ and $R^2$ are hydrogen, $C_1$–$C_{12}$-alkyl, where the substituents $R^1$ and $R^2$ together with the nitrogen atom to which they are bonded can form a 5- or 6-membered ring;

$R^5$ is hydrogen, $C_1$–$C_{12}$-alkyl, $C_3$–$C_6$-cycloalkyl.

5. A sunscreen-containing cosmetic or pharmaceutical preparation for protecting the human epidermis or human hair from UV light in the range from 280 to 400 nm, which comprises, in a cosmetically and pharmaceutically suitable carrier, amounts which are effective as photostable UV filters, of a compound of formula I

I

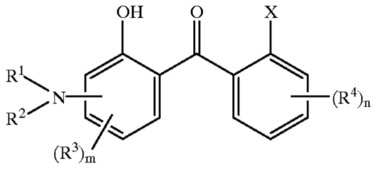

in which the variables have the meanings defined in claim 1.

6. The sunscreen-containing cosmetic or pharmaceutical preparation of claim 5, comprising, as UV-A filters, a compound of formula Ib Ib

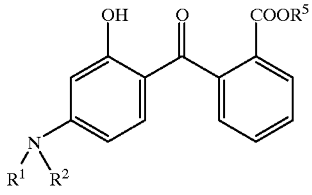

in which the substituents independently of one another have the following meanings:

$R^1$ and $R^2$ are hydrogen, $C_1$–$C_{12}$-alkyl, where the substituents $R^1$ and $R^2$ together with the nitrogen atom to which they are bonded can form a 5- or 6-membered ring;

$R^5$ is hydrogen, $C_1$–$C_{12}$-alkyl, $C_3$–$C_6$-cycloalkyl.

7. An amino-substituted hydroxybenzophenone of formula Ic,

Ic

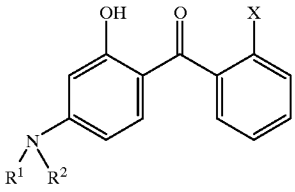

in which the variables independently of one another have the following meanings:

$R^1$ $R^2$ are hydrogen, $C_1$–$C_8$-alkyl, where the substituents $R^1$ and $R^2$ together with the nitrogen atom to which they are bonded can form a 5- or 6-membered ring;

X is $COOR^5$, $CONR^6R^7$;

$R^5$ is $C_2$–$C_{12}$-alkyl, $C_5$–$C_6$-cycloalkyl;

$R^6$ and $R^7$ are hydrogen, $C_1$–$C_{12}$-alkyl, $C_5$–$C_6$-cycloalkyl.

* * * * *

UNITED STATES PATENT AND TRADEMARK OFFICE

CERTIFICATE OF CORRECTION

PATENT NO. : 6,409,995 B1
DATED : June 25, 2002
INVENTOR(S) : Habeck et al.

It is certified that error appears in the above-identified patent and that said Letters Patent is hereby corrected as shown below:

Column 23,
Line 66, "$C_3$ 14 $C_{10}$-cycloalkyl" should be -- $C_3$-$C_{10}$-cycloalkyl --.

Signed and Sealed this

Fifteenth Day of October, 2002

*Attest:*

JAMES E. ROGAN

*Attesting Officer*

*Director of the United States Patent and Trademark Office*